(12) United States Patent
Mita et al.

(10) Patent No.: US 6,281,208 B1
(45) Date of Patent: Aug. 28, 2001

(54) THERAPEUTIC AGENT FOR GLAUCOMA

(75) Inventors: Shiro Mita, Ashiya; Eiichi Shirasawa, Kyoto, both of (JP)

(73) Assignees: Santen Pharmaceutical Co., Ltd., Osaka; Daiichi Pharmaceutical Co., Ltd., Tokyo, both of (JP)

( * ) Notice: Subject to any disclaimer, the term of this patent is extended or adjusted under 35 U.S.C. 154(b) by 0 days.

(21) Appl. No.: 08/208,497

(22) Filed: Mar. 10, 1994

Related U.S. Application Data

(63) Continuation of application No. 07/799,148, filed on Nov. 27, 1991, now abandoned.

(30) Foreign Application Priority Data

Nov. 29, 1990 (JP) .................................................... 2-333332

(51) Int. Cl.$^7$ .................................................. A61K 31/54
(52) U.S. Cl. ........................................ 514/224.2; 514/913
(58) Field of Search ................................ 514/224.2, 913

(56) References Cited

U.S. PATENT DOCUMENTS 4,786,635 * 11/1988 Iwao et al. ........................ 514/224.2

FOREIGN PATENT DOCUMENTS 0 233 291    2/1986 (EP) ........................................ 279/16
0 237 573    7/1986 (EP) ........................................ 276/16

OTHER PUBLICATIONS

Masanobu Fujita, et al., "Synthesis and Ca$^{2+}$ Antagonistic Activity of 2–[2–[(Aminoalkyl)oxy]–5–methoxyphenyl]–3, 4–dihydro–4–methyl–3–oxo–2H–1,4–benzo–thiazines," *Journal of Medicinal Chemistry*, vol. 33, No. 7, Jul. 1990, pp. 1898–1905.

Monica L. Monica, et al., "The Effect of A Calcium–Channel Blocking Agent on Intraocular Pressure," *American Journal of Ophthalmology*, Series 3, vol. 96, No. 6, Dec. 1983, p. 814.

Mark B. Abelson, et al., "Sustained Reduction of Intraocular Pressure in Humans With the Calcium Channel Blocker Verapamil," *American Journal of Ophthalmology*, vol. 105, Feb. 15, 1988, pp. 155–159.

L. Jeff Payne, et al., "Effect of Calcium Channel Blockers on Intraocular Pressure," *Ophthalmic Research*, vol. 22, No. 6, 1990, pp. 337–341.

* cited by examiner

*Primary Examiner*—Zohreh Fay
(74) *Attorney, Agent, or Firm*—Burns, Doane, Swecker & Mathis, LLP

(57) ABSTRACT

A therapeutic agent for glaucoma comprises (+)-(R)-3,4-Dihydro-2-[5-methoxy-2-[3-[N-methyl-N-[2-[(3,4-methylenedioxy) phenoxy]ethyl]amino]propoxy]phenyl]-4-methyl-3-oxo-2H-1,4-benzothiazine or its salt as active ingredient and pharmaceutically acceptable excipients. The therapeutic agent lowers the intraocular pressure upon topical or systemic administration.

15 Claims, No Drawings

THERAPEUTIC AGENT FOR GLAUCOMA

This application is a continuation of application Ser. No. 07/799,148, filed Nov. 27, 1991 now abandoned.

BACKGROUND OF THE INVENTION

The present invention relates to a therapeutic agent for glaucoma which comprises administering 2-phenyl-3-oxo-2H-1,4-benzothiazine derivative by systemic and/or topical route.

Glaucoma is an intractable eye disease caused by an elevation of intraocular pressure with various factors and a patient of glaucoma has a risk of losing his eyesight, and various medical treatments have been proposed. U.S. Pat. No. 4,786,635 discloses the use of 2-phenyl-3-oxo-2H-1,4-benzothiazine derivatives. It is described therein that these compounds have a unique structure and are useful as a therapeutic agent for circulatory diseases, since they have a calcium antagonistic effect and a blood platelet coagulation-inhibiting effect. However, any effect of these compounds on eyes has not been known.

The present inventors decided to make investigations on other effects of these compounds particularly in the ophthalmologic field.

SUMMARY OF THE INVENTION

A primary object of the present invention is to utilize the compounds in the ophthalmologic field.

Another object of the present invention is to provide a therapeutic agent for glaucoma.

Another object of the present invention is to provide a method for treating glaucoma.

These and other objects of the present invention will be apparent from the following description and Examples.

After investigations on the effects of these compounds on eyes, the inventors have found that they have an excellent effect of lowering the intraocular pressure and are useful as a therapeutic agent for glaucoma.

The present invention relates to a therapeutic agent for glaucoma which comprises, as active ingredient, a compound of the following formula (I) or its salt (hereinafter referred to as the compound of the present invention):

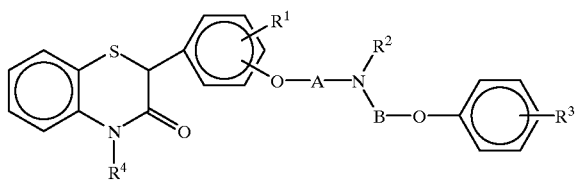

(I)

wherein $R^1$ represents one or more groups selected from the group consisting of a hydrogen atom, lower alkyl groups, halogen atoms, a nitro group, a hydroxyl group, lower alkoxy groups, lower alkanoyloxy groups, an amino group, lower alkylamino groups and lower alkoxycarbonyl groups, $R^2$ represents a hydrogen atom, a lower alkyl group or a cycloalkyl group having 3 to 6 carbon atoms, $R^3$ represents one or more groups selected from the group consisting of a hydrogen atom, lower alkyl groups, a hydroxyl group, lower alkoxy groups, halogen atoms, a nitro group, lower alkylenedioxy groups, lower alkanoyl groups, lower alkanoyloxy groups, an amino group, lower alkylamino groups, lower alkanoylamino groups and lower alkoxycarbonyloxy groups, or a group of $—(CH_2)_b—$, $R^4$ represents a hydrogen atom or a lower alkyl group, A and B may be the same or different from each other and each represents a lower alkylene group having 1 to 6 carbon atoms, and n represents 3 or 4, and pharmaceutically acceptable excipients.

DESCRIPTION OF THE PREFERRED EMBODIMENTS

In the above general formula (I), the lower alkyl groups include those having 1 to 6 carbon atoms such as methyl, ethyl, propyl and hexyl groups; the halogen atoms include fluorine, chlorine, bromine, etc.; the lower alkoxy groups include those having 1to 6 carbon atoms such as methoxy, ethoxy, propoxy and hexyloxy groups; the lower alkanoyloxy groups are those having 2 to 6 carbon atoms such as acetyloxy, propionyloxy and hexanoyloxy groups; the cycloalkyl groups having 3 to 6 carbon atoms include cyclopropyl and cyclohexyl groups, etc.; the lower alkylenedioxy groups include those having an alkylene group having 1 to 6 carbon atoms between two oxygen atoms such as methylenedioxy and ethylenedioxy groups; and the lower alkanoyl groups include those having 2 to 6 carbon atoms such as acetyl, propionyl and hexanoyl groups.

In this connection, it is preferable that $R^1$ represents a hydrogen atom or one lower alkoxy group, more preferably one lower alkoxy group, $R^2$ represents a lower alkyl group, $R^3$ represents one lower alkylenedioxy group and $R^4$ represents a lower alkyl group. Specifically, the compound represented by the following formula (II) and its salt is the most preferred:

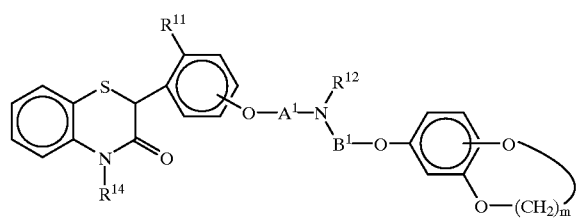

(II)

wherein $R^{11}$ represents a lower alkoxy group, $R^{12}$ represents a lower alkyl group, $R^{14}$ represents a lower alkyl group, $A^1$ and $B^1$ may be the same or different from each other and each represents a lower alkylene group having 1 to 6 carbon atoms, and m represents 1 to 6.

The salts of these compounds are not particularly limited as long as they are suitable as pharmaceuticals such as hydrochloride, sulfate, phosphate, lactate, maleate, fumarate, oxalate, methanesulfonate and p-toluenesulfonate. These compounds have stereoisomers, which are also included in the present invention.

Examples of the compounds represented by the formula [I] include, 3,4-Dihydro-2-[5-methoxy-2-[3-[N-methyl-N-[2-[(3,4-methylenedioxy)phenoxy]ethyl]amino]propoxy] phenyl]-4-methyl-3-oxo-2H-1, 4-benzothiazine fumarate, 3,4-dihydro-2-[5-methoxy-2-[4-[N-methyl-N-[2-[(3,4-methylenedioxy)phenoxy]ethyl]amino]butoxy]phenyl]-4-methyl-3 -oxo-2H-1,4-benzothiazine oxalate, 3,4-dihydro-2-[2-[4-[N-[2-(4-methoxyphenoxy)ethyl]-N-methylamino] butoxy]-5-methoxyphenyl]-4-methyl-3-oxo-2H 1,4-benzothiazine oxalate, 3,4-dihydro-2-[5-methoxy-2-[3-[N-methyl-N-[2-[(3,4,5-trimethoxy)phenoxy]ethyl]amino] propoxy]phenyl]-4-methyl-3-oxo-2H,-1,4-benzothiazine oxalate, 3,4-dihydro-2-[4-[3-N-methyl-N-[2-[(3,4- methylenedioxy)phenoxy]ethyl]amino]propoxy]phenyl]-4-methyl-3-oxo-2H-1,4-benzothiazine oxalate, 3,4-dihydro-2-[5-methoxy-2-[2-[N-methyl-N-[2-[(3,4-methylenedioxy)phenoxy]ethyl]amino]ethoxy]phenyl]-4-methyl-3-oxo-2H-1,4-benzothiazineoxolate, 3,4-dihydro-2-[5-chloro-2-[3-[N-methyl-N-[2-[(3,4-methylenedioxy)phenoxy]ethyl]amino]propoxyl]-phenyl]-4-methyl-3-oxo-2H-1,4-benzothiazine fumarate, 3,4-dihydro-2-[2-[4-[N-[2-[(5-indanyloxy)ethyl]-N-methylamino]butoxy]-5-methoxyphenyl]-4-methyl-3-oxo-2H-1,4-benzothiazine oxalate, 3,4-dihydro-2-[5-methyl-2-[3-[N-methyl-N-[2-[(3,4-methylenedioxy)phenoxy]ethyl]amino]propoxy]-phenyl]-4-methyl-3-oxo-2H-1,4-benzothiazine fumarate, 3,4-dihydro-2-[[3-[N-methyl-N-[2-[(3,4-methylenedioxy)phenoxy]ethyl]amino]propoxy]-5-nitrophenyl]-4-methyl-3-oxo-2H-1,4-benzothiazine fumarate, their stereoisomers and optical isomers.

Although the compounds of the present invention are useful as an effective therapeutic agent for circulatory diseases, the effect of them on eyes has never been known.

After investigations made for the purpose of using these compounds in the field of ophthalmology, the inventors have found that they have an excellent effect of lowering the intraocular pressure and, therefore, they are useful as a therapeutic agent for glaucoma.

To evaluate the utility of the compounds of the present invention for the treatment of glaucoma, the effect of them on rabbits having a high intraocular pressure provoked by chymotrypsin was examined.

The detailed data will be described below with reference to the physiological tests. When the compound of the present invention was given by instillation or oral administration, the intraocular pressure was reduced to indicate that this compound is useful as a therapeutic agent for glaucoma.

The therapeutic agent for glaucoma of the present invention can be used as either an agent for topical application such as eye drops or eye ointment or a systemic one such as tablets, capsules, granules and powders. Further they can be used in combination.

The dose of the compound of the present invention can be suitably determined depending on the symptoms, age, dosage form, etc. In the topical application, a solution or an ointment having a concentration of 0.1 to 5%, more preferably 0.1 to 2%, is applied once to several times a day and, in the systemic application, it is applied once to several times a day in an amount of preferably 1 to 1000 mg, more preferably 1 to 100 mg a day.

The preparation containing the compound of the present invention can be produced by adding necessary excipients to the compound by an ordinary method. For example, eye drops can be produced by adding an isotonizing agent such as sodium chloride, potassium chloride or concentrated glycerol; buffering agent such as sodium phosphate, boric acid or monoethanolamine; stabilizer such as sodium edetate; preservative such as benzalkonium chloride or p-hydroxybenzoate; surfactant such as polysorbate 80 or polyoxyethylene hydrogenated castor oil; and pH adjustor such as dilute hydrochloric acid or sodium hydroxide, if necessary. The therapeutic agent for the systemic administration such as tablets, capsules, granules and powders can be produced by adding diluent such as lactose, starch or crystalline cellulose; lubricant such as magnesium stearate or talc; binder such as hydroxypropyl cellulose or polyvinylpyrrolidone; disintegrant such as carboxymethylcellulose calcium or low substituted hydroxypropylcellulose and coating agent such as hydroxypropyl methylcellulose, macrogol or silicone resin, if necessary.

Typical formulations of the oral preparations and ophthalmics will be given below.

As for the preparations for oral administration, some examples are also disclosed in U.S. Pat. No. 4,786,635.

EXAMPLES OF FORMULATIONS

1) Eye Drops:
Formulation 1 (for 100 ml)
(−)-(R)-3,4-Dihydro-2-[5-methoxy-2-[3-[N-methyl-N-[2-[(3,4-methylenedioxy)phenoxy]ethyl]amino]-propoxy]phenyl]-4-methyl-3-oxo-2H-1,4-benzothiazine

[Examples of formulations]

1) Eye drops:

| | |
|---|---|
| Formulation 1 (for 100 ml) | |
| (+)−(R)−3,4-Dihydro-2-[5-methoxy-2-[3-[N-methyl-N-[2-[(3,4-methylenedioxy)phenoxy]ethyl]amino]-propoxy]phenyl]-4-methyl-3-oxo-2H-1,4-benzothiazine fumarate | 0.5 g |
| Concentrated glycerol | 1.5 g |
| Polyoxyethylene hydrogenated castor oil | 1.0 g |
| Benzalkonium chloride | 0.005 g |
| Sodium edetate | 0.01 g |
| Dilute hydrochloric acid | q.s. |
| Sodium hydroxide | q.s. |
| Sterile, purified water | q.s. |
| Formulation 2 | |
| (+)−(R)−3,4-Dihydro-2-[5-methoxy-2-[3-[N-methyl-N-[2-[(3,4-methylenedioxy)phenoxy]ethyl]amino]-propoxy]phenyl]-4-methyl-3-oxo-2H-1,4-benzothiazine fumarate | 1.0 g |
| Concentrated glycerol | 1.25 g |
| Polysorbate 80 | 2.0 g |
| Methyl p-hydroxybenzoate | 0.026 g |
| Propyl p-hydroxybenzoate | 0.014 g |
| Dilute hydrochloric acid | q.s. |
| Sodium hydroxide | q.s. |
| Sterile, purified water | q.s. |
| Formulation 3 (for 100 ml) | |
| (+)−(R)−3,4-Dihydro-2-[5-methoxy-2-[3-[N-methyl-N-[2-[(3,4-methylenedioxy)phenoxy]ethyl]amino]-propoxy]phenyl]-4-methyl-3-oxo-2H-1,4-benzothiazine fumarate | 0.1 g |
| Concentrated glycerol | 2.0 g |
| Polyoxyethylene hydrogenated castor oil | 0.8 g |
| Benzalkonium chloride | 0.005 g |
| Sodium edetate | 0.01 g |
| Dilute hydrochloric acid | q.s. |
| Sodium hydroxide | q.s. |
| Sterile, purified water | q.s. |
| 2) Eye ointment: | |
| Formulation 1 (for 100 g) | |
| (+)−(R)−3,4-Dihydro-2-[5-methoxy-2-[3-[N-methyl-N-[2-[(3,4-methylenedioxy)phenoxy]ethyl]amino]-propoxy]phenyl]-4-methyl-3-oxo-2H-1,4-benzothiazine fumarate | 1.0 g |
| Liquid paraffin | 10 g |
| White petrolatum | 89 g |
| Formulation 2 (for 100 g) | |
| (+)−(R)−3,4-Dihydro-2-[5-methoxy-2-[3-[N-methyl-N-[2-[(3,4-methylenedioxy)phenoxy]ethyl]amino]-propoxy]phenyl]-4-methyl-3-oxo-2H-1,4-benzothiazine fumarate | 2.0 g |
| Liquid paraffin | 10 g |
| White petrolatum | 88 g |
| 3) Tablet: | |
| Formulation 1 (for 100 mg) | |
| (+)−(R)−3,4-Dihydro-2-[5-methoxy-2-[3-[N-methyl-N-[2-[(3,4-methylenedioxy)phenoxy]ethyl]amino]-propoxy]phenyl]-4-methyl-3-oxo-2H-1,4-benzothiazine fumarate | 1 mg |
| Lactose | 66.4 mg |
| Corn starch | 20 mg |

-continued

[Examples of formulations]

| | |
|---|---|
| Carboxymethylcellulose calcium | 6 mg |
| Hydroxypropylcellulose | 4 mg |
| Magnesium stearate | 0.6 mg |

The above tablet is film coated with 2 mg of ordinal coating agents such as hydroxypropyl methylcellulose, macrogol and silicone resin to prepare the desired tablet (the following formulations are treated by the same manner).

| | |
|---|---|
| Formulation 2 (for 100 mg) | |
| (+) − (R) − 3,4-Dihydro-2-[5-methoxy-2-[3-[N-methyl-N-[2-[(3,4-methylenedioxy)phenoxy]ethyl]amino]-propoxy]phenyl]-4-methyl-3-oxo-2H-1,4-benzothiazine fumarate | 5 mg |
| Lactose | 62.4 mg |
| Corn starch | 20 mg |
| Carboxymethylcellulose calcium | 6 mg |
| Hydroxypropylcellulose | 4 mg |
| Magnesium stearate | 0.6 mg |
| Coating agent | 2 mg |
| Formulation 3 (for 100 mg) | |
| (+) − (R) − 3,4-Dihydro-2-[5-methoxy-2-[3-[N-methyl-N-[2-[(3,4-methylenedioxy)phenoxy]ethyl]amino]-propoxy]phenyl]-4-methyl-3-oxo-2H-1,4-benzothiazine fumarate | 20 mg |
| Lactose | 51 mg |
| Corn starch | 15 mg |
| Carboxymethylcellulose calcium | 5 mg |
| Hydroxypropylcellulose | 5 mg |
| Magnesium stearate | 1 mg |
| Talc | 1 mg |
| Coating agent | 2 mg |
| Formulation 4 (for 100 mg) | |
| (+) − (R) − 3,4-Dihydro-2-[5-methoxy-2-[3-[N-methyl-N-[2-[(3,4-methylenedioxy)phenoxy]ethyl]amino]-propoxy]phenyl]-4-methyl-3-oxo-2H-1,4-benzothiazine fumarate | 40 mg |
| Lactose | 34 mg |
| Corn starch | 10 mg |
| Carboxymethylcellulose calcium | 5 mg |
| Hydroxypropylcellulose | 5 mg |
| Magnesium stearate | 2 mg |
| Talc | 2 mg |
| Coating agent | 2 mg |
| Formulation 5 (for 100 mg) | |
| (+) − (R) − 3,4-Dihydro-2-[5-methoxy-2-[3-[N-methyl-N-[2-[(3,4-methylenedioxy)phenoxy]ethyl]amino]-propoxy]phenyl]-4-methyl-3-oxo-2H-1,4-benzothiazine fumarate | 80 mg |
| Lactose | 69 mg |
| Corn starch | 20 mg |
| Carboxymethylcellulose calcium | 10 mg |
| Hydroxypropylcellulose | 10 mg |
| Magnesium stearate | 4 mg |
| Talc | 4 mg |
| Coating agent | 3 mg |

[Pharmacological Test]

For evaluation of the effect of a medicine for the treatment of glaucoma, a method wherein it is administered to rabbits having a high intraocular pressure provoked by chymotrypsin is known [Vareilles, P. et al., Invest. Ophthalmol. 16, 987 (1977)].

(+)-(R)-3,4-Dihydro-2-[5-methoxy-2-[3-[N-methyl-N-[2-[(3,4-methylenedioxy)phenoxy]ethyl]amino]propoxy]phenyl]-4-methyl-3-oxo-2H-1,4-benzothiazine fumarate was used as a typical example of the compounds of the present invention. It was given to the subjects by topical administration or oral administration to examine its effects.

1. Effect of Instillation:
(Experimental Method)
Rabbits having a high intraocular pressure (29 to 49 mm Hg) provoked by giving α-chymotrypsin at least one year before they were used in the tests according to a method of Sears et al. [Am. J. Ophthalmol.77, 378 (1974)]. 50 μl of the eye drops of Formulation 2 in the Examples was applied to both eyes of each rabbit and the intraocular pressure thereof was determined before the application and 0.5, 1, 2, 3 and 4 hours after the application. The intraocular pressure was determined by applying 0.4% hydroxyprocaine hydrochloride to both eyes of the rabbit while it was lightly holded to conduct the topical anesthetization and measuring the pressure with a pneumatic tonometer.
(Results)
The intraocular pressure was obserbed to be lower than that determined immediately before the application of the compound of the present invention by 2.8 mmHg after 2 hours and by 2.2 mm Hg after 3 hours.

2. Effects Obtained by Oral Administration:
(Method of Experiment)
The experiment was conducted in the same manner as that described above. The compound of the present invention was suspended in 0.5% methyl cellulose and given in an amount of 3 mg/kg or 30 mg/kg by oral administration.
(Results)
The intraocular pressure was lower than that determined immediately before the oral administration of the compound of the present invention by 2.3 mmHg after 1 hour, by 3.1 mm Hg after 2 hours and by 3.0 mm Hg after 3 hours in the group to which 3 mg/kg of the compound had been administered; and by 4.5 mm Hg after 1 hour, 4.8 mm Hg after 2 hours and 5.5 mm Hg after 3 hours in the group to which 30 mg/kg of the compound had been administered.

It will be apparent from the above-described experimental results that when the compound of the present invention is administered, the intraocular pressure is clearly lowered.

As shown in the pharmacological tests, the compounds of the present invention have an excellent intraocular pressure-lowering effect and are useful as a therapeutic agent for glaucoma.

What is claimed is:

1. A method for treating glaucoma which comprises administering an effective amount of a therapeutic agent for glaucoma comprising, as active ingredient, a compound of the following formula (I) or its salt:

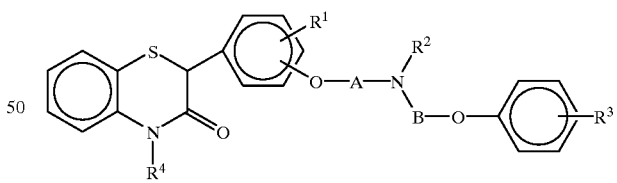

wherein $R^1$ represents one or more groups selected from the group consisting of a hydrogen atom, lower alkyl groups, halogen atoms, a nitro group, a hydroxyl group, lower alkoxy groups, lower alkanoyloxy groups, an amino group, lower alkylamino groups and lower alkoxycarbonyl groups, $R^2$ represents a hydrogen atom, a lower alkyl group or a cycloalkyl group having 3 to 6 carbon atoms, $R^3$ represents one or more groups selected from the group consisting of a hydrogen atom, lower alkyl groups, a hydroxyl group, lower alkoxy groups, halogen atoms, a nitro group, lower alkylenedioxy groups, lower alkanoyl groups, lower alkanoyloxy groups, an amino group, lower alkylamino groups, lower alkanoylamino groups and lower alkoxycarbonyloxy groups, or a group of —(CH$_2$)$_b$—, R$^4$ represents a hydrogen atom or a lower alkyl group, A and B may be the same or different from each other and each represent a lower alkylene group having 1 to 6 carbon atoms, and n represents 3 or 4, and pharmaceutically acceptable diluent and/or carrier to a patient suffering from glaucoma.

2. A method of claim 1 in which R$^1$ represents a hydrogen atom or one lower alkoxy group, R$^2$ represents a lower alkyl group, R$^3$ represents one lower alkylenedioxy group and R$^4$ represents a lower alkyl group.

3. A method of claim 2 in which the lower alkoxy group, lower alkyl group and lower alkylenedioxy group have 1 to 6 carbon atoms, respectively.

4. A method of claim 2 in which R$^1$ represents one lower alkoxy group.

5. A method of claim 4 in which the compound is represented by the following formula (II) or its salt:

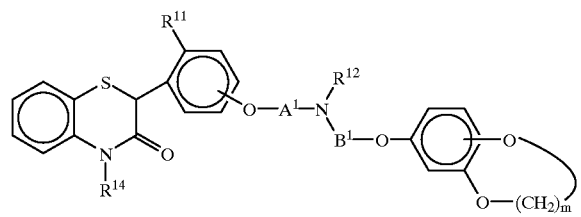

(II)

wherein R$^{11}$ represents a lower alkoxy group, R$^{12}$ represents a lower alkyl group, R$^{14}$ represents a lower alkyl group, A$^1$ and B$^1$ may be the same or different from each other and each represents a lower alkylene group having 1 to 6 carbon atoms, and m represents 1 to 6.

6. A method of claim 5 in which the compound is (+)-(R)-3,4-Dihydro-2-[5-methoxy-2-[3-[N-methyl-N-[2-[(3,4-methylenedioxy) phenoxy]ethyl]amino]propoxy]phenyl]-4-methyl-3-oxo-2H-1,4-benzothiazine or its salt.

7. A method of claim 1 wherein the therapeutic agent for glaucoma is topically administered to the patient.

8. A method of claim 7 wherein the therapeutic agent is topically administered using eye drops or eye ointment.

9. A method of claim 8 wherein the therapeutic agent has a concentration of active ingredient of 0.1 to 5%.

10. A method of claim 9 wherein the therapeutic agent has a concentration of active ingredient of 0.1 to 2%.

11. A method of claim 1 wherein the therapeutic agent for glaucoma is systemically administered to the patient.

12. A method of claim 11 wherein the therapeutic agent is systemically administered using tablets, capsules, granules or powders.

13. A method of claim 12 wherein the effective amount of active ingredient administered to the patient per day is 1 to 1000 mg.

14. A method of claim 13 wherein the effective amount of active ingredient administered to the patient per day is 1 to 100 mg.

15. A method of claim 1 wherein the therapeutic agent is administered to the patient by a combination of topical and systemic administration.

* * * * *